(12) United States Patent
Ashida et al.

(10) Patent No.: US 8,637,572 B2
(45) Date of Patent: Jan. 28, 2014

(54) COMPOSITION FOR PROMOTING COLLAGEN PRODUCTION

(75) Inventors: Yutaka Ashida, Yokohama (JP); Yosuke Tojo, Yokohama (JP); Shoichiro Shimada, Yokohama (JP); Chieko Mizumoto, Yokohama (JP); Masashi Mita, Tokyo (JP)

(73) Assignee: Shiseido Company, Ltd., Tokyo (JP)

( * ) Notice: Subject to any disclaimer, the term of this patent is extended or adjusted under 35 U.S.C. 154(b) by 0 days.

(21) Appl. No.: 13/261,238

(22) PCT Filed: Sep. 27, 2010

(86) PCT No.: PCT/JP2010/066672
§ 371 (c)(1),
(2), (4) Date: Mar. 28, 2012

(87) PCT Pub. No.: WO2011/040363
PCT Pub. Date: Apr. 7, 2011

(65) Prior Publication Data
US 2012/0184619 A1     Jul. 19, 2012

(30) Foreign Application Priority Data

Sep. 29, 2009   (JP) ................................ 2009-224743
Sep. 30, 2009   (JP) ................................ 2009-225870

(51) Int. Cl.
*A01N 37/12*          (2006.01)
(52) U.S. Cl.
USPC ............ 514/561; 514/380; 514/423; 514/562
(58) Field of Classification Search
USPC ..................... 464/62; 514/380, 561, 562, 423
See application file for complete search history.

(56) References Cited

U.S. PATENT DOCUMENTS

2008/0260672 A1    10/2008   Oshimura et al.

FOREIGN PATENT DOCUMENTS

| CN | 1107335 A | 8/1995 |
|---|---|---|
| JP | 07-194375 A | 8/1995 |
| JP | 2005-003558 A | 1/2005 |
| JP | 2007-051087 A | 3/2007 |
| JP | 2008-185558 A | 8/2008 |

OTHER PUBLICATIONS

Tetsuji et al, JP1999-060436, published Mar. 2, 1999, Machine Translation.*
Kinya et al, JP2005-029486, published Feb. 3, 2005, Machine Translation.*
Wilson et al, J Bid Chem, 1930, 85, 559-569.*
Kajiro, Y., Ed., "Amino Acids," Harper's Biochemistry, $22^{nd}$ Edition, Maruzen Co. Ltd., Tokyo, Mar. 30, 1991, 21-30, with partial English translation of indicated portions, 2 pages.
Kinouchi et al., "D-Amino acid biosystem in mammal," Protein, Nucleic Acids and Enzymes, 2005, 50(5):453-460, with partial English translation of indicated portion, 1 page.
Kligman et al., "Effects of topical tretinoin on non-sun-exposed protected skin of the elderly," J. Am. Acad. Dermatol., 1993, 29:25-33.
Kligman et al., "Topical tretinoin for photoaged skin," J. Am. Acad. Dermatol., 1986, 15:836-859.
Morikawa et al., "Alterations in D-amino acid levels in the brains of mice and rats after the administration of D-amino acids," Amino Acids, 2007, 32:13-20.
Mukherjee et al., "Retinoids in the treatment of skin aging: an overview of clinical efficacy and safety," Clinical Interventions in Aging, 2006, 1(14):327-348.
Takeda et al., "Similar, but Not Identical, Modulation of Expression of Extracellular Matrix Components During In Vitro and In Vivo Aging of Human Skin Fibroblasts," Journal of Cellular Physiology, 1992, 153:450-459.
Varani et al., "Decreased Collagen Production in Chronologically Aged Skin," American Journal of Pathology, Jun. 2006, 168(6):1861-1868.
Varani et al., "Inhibition of Type I Procollagen Synthesis by Damaged Collagen in Photoaged Skin and by ollagenase-Degraded Collagen in Vitro," American Journal of Pathology, Mar. 2001, 158(3):931-942.
Yamashina et al., "Amino Acids, Peptides, and Proteins," Principles of Biochemistry, $2^{nd}$ Ed., Hirokawa Publishing Co., Tokyo, Apr. 15, 1993, 132-147, with partial English translation of indicated portion, 1 page.

* cited by examiner

*Primary Examiner* — Jason M Sims
*Assistant Examiner* — Ibrahim D Bori
(74) *Attorney, Agent, or Firm* — Foley & Lardner LLP

(57) ABSTRACT

Disclosed is a novel composition which has an effect on promoting production of collagen. The composition has high photostability and is free from side effects such as those of retinoids. Specifically disclosed is a composition for promoting collagen production which contains one or more compounds selected from the group consisting of D-aspartic acid, D-alanine, derivatives and/or salts thereof. The composition may be used for the purpose of suppressing and/or improving skin a condition. The skin condition may include but is not limited to photoaging and/or wrinkles. The composition may be used for an external preparation for the skin or food. The composition may be a composition for promoting type I collagen production.

3 Claims, 3 Drawing Sheets

COMPOSITION FOR PROMOTING COLLAGEN PRODUCTION

CROSS-REFERENCE TO RELATED APPLICATIONS

This application is a National Stage application of PCT/JP2010/066672, filed Sep. 27, 2010, which claims priority from Japanese applications JP 2009-224743, filed Sep. 29, 2009 and JP 2009-225870, filed Sep. 30, 2009.

TECHNICAL FIELD

The present invention relates to a composition for promoting collagen production which comprising one or more compounds selected from the group consisting of D-aspartic acid, D-alanine, derivatives and/or salts thereof, and a method of suppressing and/or improving a skin condition comprising a step of administering the compound.

BACKGROUND ART

Type I collagen is one of the major skin proteins and it is a triple helix protein composed of two strands of α(alpha)1 (I) chain and one strand of α(alpha) 2 (I) chain. Type I collagen is produced by fibroblasts in the skin dermis and it forms an extracellular matrix in which the fibroblasts are embedded. Both intrinsic aging and photoaging are accompanied with reduced collagen production and increased activity of collagenase (Non-Patent Documents 1 to 3). Thus, it has been believed that a promotion of collagen production leads to suppression and/or improvement of a skin condition caused by intrinsic aging or photoaging, for example, wrinkle formation. In fact, it is known that retinoids, i.e., derivatives of vitamin A, have an efficacy when applied to the face or upper arm skin caused by intrinsic aging or photoaging (Non-Patent Documents 4 and 5). However, the retinoids have a side effect like photosensitization or inflammatory reaction known as a retinoid reaction (Non-Patent Document 6). Further, having generally high photoreactivity, the retinoids need to be protected from light for stable storage. Thus, after administration to the skin, the retinoids may be easily decomposed by light penetrating a living body under ordinary living conditions.

PRIOR ART DOCUMENTS

Non-Patent Document

Non-Patent Document 1: Takeda, K. et al., J. Cell. Physiol., 153:450 (1992)
Non-Patent Document 2: Varani, J. et al., Am. J. Pathol., 158:931 (2001)
Non-Patent Document 3: Varani, J. et al., Am. J. Pathol., 168:1861 (2006)
Non-Patent Document 4: Kligman, A. M. et al., J. Am. Acad. Dermatol., 15:836 (1986)
Non-Patent Document 5: Kligman, A. M. et al., J. Am. Acad. Dermatol., 29:25 (1993)
Non-Patent Document 6: Mukherjee, S. et al., Clin. Interv. Aging 1:327 (2006)

DISCLOSURE OF THE INVENTION

Problem to be Solved by the Invention

Under the circumstances, there is a need to develop a novel composition which has an effect on promoting collagen production, specifically a composition which has high photostability and is free from side effects such as those of retinoids.

Means for Solving the Problem

The present invention provides a composition for promoting collagen production comprising one or more compounds selected from the group consisting of D-aspartic acid, D-alanine, derivatives and/or salts thereof.

The composition for promoting collagen production of the present invention may be used for suppressing and/or improving a skin condition.

Regarding the composition for promoting collagen production of the present invention, the skin condition comprises photoaging and/or wrinkles, but not limited thereto.

The composition for promoting collagen production of the present invention may be used for an external preparation for the skin.

The composition for promoting collagen production of the present invention may be used for a food.

The composition for promoting collagen production of the present invention may be a composition for promoting type I collagen production.

The present invention also provides a method of suppressing and/or improving a skin condition comprising a step of administering a composition for promoting collagen production comprising one or more compounds selected from the group consisting of D-aspartic acid, D-alanine, derivatives and/or salts thereof.

The skin condition that is suppressed and/or improved by the method of the present invention comprises photoaging and/or wrinkles, but not limited thereto.

Regarding the method of the present invention, the composition for promoting collagen production of the present invention may be used for an external preparation for the skin.

Regarding the method of the present invention, the composition for promoting collagen production of the present invention may be used for a food composition.

According to the Method of the present invention, the composition for promoting collagen production may be a composition for promoting type I collagen production.

As used herein, the term "salt" of D-aspartic acid and D-alanine indicates any salts comprising a metal salt and an amine salt or the like, provided that the effect on promoting collagen production of D-aspartic acid and D-alanine is not impaired. The metal salts may comprise an alkaline metal salt, an alkaline earth metal salt and the like. The amine salts may comprise a triethylamine salt, a benzylamine salt and the like.

As used herein, the term "derivatives" of D-aspartic acid and D-alanine indicates D-aspartic acid and D-alanine molecules that are covalently bound to any atomic group via their amino groups, carboxyl groups, or side chains, provided that the effect on promoting collagen production of D-aspartic acid and D-alanine is not impaired. The atomic group includes, but is not limited to, protective groups, such as N-phenylacetyl group, and 4,4'-dimethoxytrityl (DMT) group; biopolymers, such as a protein, a peptide, a saccharide, a lipid, and a nucleic acid; synthetic polymers, such as a polystyrene, a polyethylene, a polyvinyl, and a polyester; and functional groups such as an ester group. The ester group may comprise, for example, an aliphatic ester, such as methyl ester, and ethyl ester; and an aromatic ester.

An amino acid has optical isomers which are the L-form and D-form. A natural protein has L-amino acids bound by peptide bonds and only L-amino acids are employed excluding some exceptions such as a bacterial cell wall. Therefore, it has been considered that in a mammal including a human only L-amino acids are present and only L-amino acids are utilized (Kinouchi, T. et al., TANPAKUSHITSU KAKUSAN KOSO (PROTEIN, NUCLEIC ACID AND ENZYME), 50:453-460 (2005), Lehninger Principles of Biochemistry [Vol. 1] 2nd ed., pp 132-147 (1993), Japanese-language translation, Hirokawa Shoten Ltd., Harper's Biochemistry, Original version, 22nd ed., pp 21-30 (1991), Japanese-language translation Maruzen Co., Ltd.). Accordingly, only L-amino acids have been mostly employed as amino acids academically and industrially for a long time.

Exceptional cases where a D-amino acid is employed are, for example, a case of using as a raw material for an antibiotics produced by a microorganism, and, a case of a food additive employing a D-amino acid in a DL-amino acid mixture for the purpose of reducing cost of fractionating only an L-amino acid from a mixture of the L- and D-amino acids, which are obtained in equimolar amounts by synthesizing the amino acids. Nevertheless, there has been no case of using only a D-amino acid not including an L-amino acid industrially as a physiologically active substance.

D-serine and D-aspartic acid have high ratio of D-form, and therefore many studies have been made compared to other amino acids. D-serine is localized in the cerebrum and the hippocampus, and it is known as a regulatory factor for the NMDA receptor in the brain. D-aspartic acid is found to be localized in the testis and pineal body, and it is known to be involved in the control of hormone secretion (Japanese Patent Unexamined Publication No. 2005-3558). However, the physiological activities of D-aspartic acid and D-alanine in the skin are not clearly defined.

As illustrated in the following examples, the effect on promoting collagen production of D-aspartic acid and D-alanine has been unknown so far. Thus, the composition for promoting collagen production of the present invention comprising D-aspartic acid and/or D-alanine is a novel invention.

Recently, it was reported that ddY mice were allowed to ingest freely a 10 mM aqueous solution of a D-amino acid for two weeks and then examined for the D-amino acid concentration in each organ, which was 3 to 1000 pmol per gland in the pineal body and 2 to 500 nmol per wet gram in the brain tissue (Morikawa, A. et al., Amino Acids, 32:13-20 (2007)). Based on the above, the lower limit for daily intake amount of D-aspartic acid and D-alanine contained in the composition of the present invention is calculated as described below.

The D-aspartic acid of the present invention has an effect on promoting collagen production in cultured human fibroblasts within the concentration range of 0.01 μM (micro-molar) to 320 μM (micro-molar), as described in the following Examples. Thus, the amount of the D-aspartic acid that is contained in the composition of the present invention may be any content, provided that the D-aspartic acid in the above concentration range is delivered to fibroblasts in the skin tissue in vivo. As for an external preparation for the skin of the present invention, the content of D-aspartic acid may be 0.0000001% by weight to 50% by weight, or up to the maximum weight concentration that can be formulated, in the total composition of the invention. Specifically, when the composition is an external preparation for the skin, the content of D-aspartic acid is preferably 0.000001% by weight to 30% by weight, and the most preferably 0.00001% by weight to 3% by weight. When the composition of the present invention is an internal agent, the content of D-aspartic acid may be within the range of 0.0000001% by weight to 100% by weight. When the composition of the present invention is an internal agent, the content of the D-aspartic acid is preferably 0.0000002% by weight to 80% by weight and the most preferably 0.000001% by weight to 60% by weight. Further, the lower limit of a daily intake amount of D-aspartic acid that is contained in the composition of the present invention may be 0.01 ng, preferably 0.1 ng, and more preferably 1 ng per 1 kg of body weight.

As illustrated in the following examples, within the concentration range of from 0.01 μM (micro-molar) to 1000 μM (micro-molar), D-alanine of the present invention has an effect on promoting collagen production in cultured human fibroblasts. As such, the amount of D-alanine contained in the skin condition improving agent, an external preparation for the skin, and the food composition of the present invention can have any amount, provided that the D-alanine within the above concentration range is delivered to fibroblasts in the skin tissue in vivo. As for an external preparation for the skin of the present invention, the content of D-alanine may be from 0.000001% by weight to 50% by weight, or up to the maximum weight concentration that can be formulated, in the total composition of the invention. Specifically, when the composition is an external preparation for the skin, the content of D-alanine is preferably 0.00001% by weight to 30% by weight, and the most preferably 0.0001% by weight to 10% by weight. When the composition of the present invention is an internal agent, the content of D-alanine may be within the range of 0.000001% by weight to 100% by weight. When the composition of the present invention is an internal agent, the content of D-alanine is preferably 0.00001% by weight to 80% by weight and the most preferably 0.0001% by weight to 60% by weight. Further, the lower limit of a daily intake amount of D-alanine that is contained in the composition of the present invention may be 0.01 ng, preferably 0.1 ng, and more preferably 1 ng per 1 kg of body weight.

The composition of the present invention may further comprise one or more pharmaceutically acceptable additives, in addition to the group of D-aspartic acid, D-alanine, salts of D-aspartic acid and D-alanine and/or derivatives of D-aspartic acid and D-alanine capable of releasing D-aspartic acid and D-alanine by a drug metabolizing enzyme and the like in vivo, provided that the effect on promoting collagen production of D-aspartic acid and D-alanine is not impaired. Such additives comprise, but are not limited to, a diluent and an extender, a binder and an adhesive, a lubricant, a glidant, a plasticizer, a disintegrant, a carrier solvent, a buffering agent, a colorant, a flavoring agent, a sweetener, a preservative and a stabilizer, an adsorbent, as well as other pharmaceutical additives known to those skilled in the art.

The composition of the present invention may be prepared by using, as an active component, only D-aspartic acid, D-alanine, salts of D-aspartic acid and D-alanine and/or derivatives of D-aspartic acid and D-alanine capable of releasing D-aspartic acid and D-alanine by a drug metabolizing enzyme and the like in vivo. However, within the range that the effect of the present invention is not impaired, it may be appropriately formulated with other components that are used for an external preparation for the skin like cosmetics comprising quasi drugs and pharmaceutical products, if necessary. Examples of other components (i.e., optionally formulated components) comprise an oil, a surface active agent, a powder, a colorant, water, alcohols, a thickening agent, a chelating agent, silicones, an antioxidant, an UV absorbing agent, a moisturizing agent, a flavoring agent, various pharmaceutically active ingredients, a preservative, a pH adjusting agent, and a neutralizing agent.

A dosage form of a composition of promoting collagen production of the present invention that is used for suppressing and/or improving a skin condition (herein below, referred to as an "agent for improving skin condition") may be any one that is commonly used for quasi drug compositions and pharmaceutical compositions comprising an external preparation for the skin like an ointment, a cream, an emulsion, a lotion, a pack, gel, and a patch, an oral preparation like powder, granules, a soft capsule, and a tablet, a pernasal preparation like a nasal spray, and an injection solution.

A dosage form of the external preparation for the skin according to the present invention is not specifically limited, provided that it is conventionally used for an external preparation for the skin, and it comprises an ointment, a cream, an emulsion, a lotion, a pack, a gel, and a patch.

The food composition of the present invention may further comprise, in addition to D-aspartic acid, D-alanine, salts of D-aspartic acid and D-alanine and/or derivatives of D-aspartic acid and D-alanine capable of releasing D-aspartic acid and D-alanine by a drug metabolizing enzyme and the like in vivo, a seasoning, a colorant, a preservative, and other components that can be used for a food product, provided that the effect on promoting collagen production by D-aspartic acid and D-alanine is not impaired.

The food composition of the present invention may be any one employed conventionally as a food composition comprising, but not limited to, a candy, a cookie, bean paste, a French dressing, a mayonnaise, a French bread, a soy sauce, yogurt, dried seasoning powder for rice, seasoning/sauce for natto (Japanese fermented soybean), natto, unrefined black vinegar.

DESCRIPTION OF EMBODIMENTS

Examples of the present invention described below are intended only to exemplify the present invention rather than to limit the technical scope thereof. The technical scope of the present invention is limited only by the descriptions in the claims.

All references cited herein are incorporated by reference in its entirety.

Example 1

Collagen Production Promoting Effect of D-Aspartic Acid Methods

Cell Culture

Commercially available human neonatal dermal fibroblasts (Cryo NHDF-Neo, manufactured by Sanko Junyaku Co., Ltd.) were used. The cells were inoculated in a commercially available 24-well plate to have $2 \times 10^5$ cells per well. The cells were then cultured for four hours in a commercially available medium for cell culture (D-MEM (1 g/L glucose), manufactured by Wako Pure Chemical Industries, Ltd.) to which 10% bovine fetal serum was supplemented (herein below, referred to as a "standard medium") in a 5% $CO_2$ and saturated water vapor atmosphere at 37° C. (degrees Celsius).

Addition of Amino Acids

Subsequently, the medium was switched to a commercially available medium for cell culture (D-MEM (1 g/L glucose), manufactured by Wako Pure Chemical Industries, Ltd.) supplemented with 0.5% bovine fetal serum (herein below, referred to as "low-serum medium") and cultured for approximately one day in a 5% $CO_2$ and saturated water vapor atmosphere at 37° C. (degrees Celsius). D-aspartic acid (manufactured by Wako Pure Chemical Industries, Ltd., 018-04821) was added to the low-serum medium to have the concentration of 0.01 μM (micro-molar), 0.1 μM (micro-molar), μM (micro-molar), 100 μM (micro-molar), or 320 μM (micro-molar). As a positive control, magnesium L-ascorbyl phosphate (L-Ascorbic Acid Phosphate Magnesium Salt n-Hydrate, herein below, referred to as "APM", manufactured by Wako Pure Chemical Industries, Ltd., 013-19641) was added to the low-serum medium to have the concentration of 150 μM (micro-molar), 250 μM (micro-molar), or 500 μM (micro-molar). Further, the low-serum medium described above to which neither APM nor D-aspartic acid had been added was employed as a negative control.

Quantification of Production Amount of Type I Collagen

After completing the cell culture for two days, the culture supernatant was collected and the concentration of C-terminal peptide of type I procollagen (herein below, referred to as "PIP") produced by human neonatal dermal fibroblasts was measured by using Procollagen type I C-peptide EIA kit (manufactured by Takara Bio Inc.) according to the manufacturer's instruction.

Quantification Results

Figure 1:
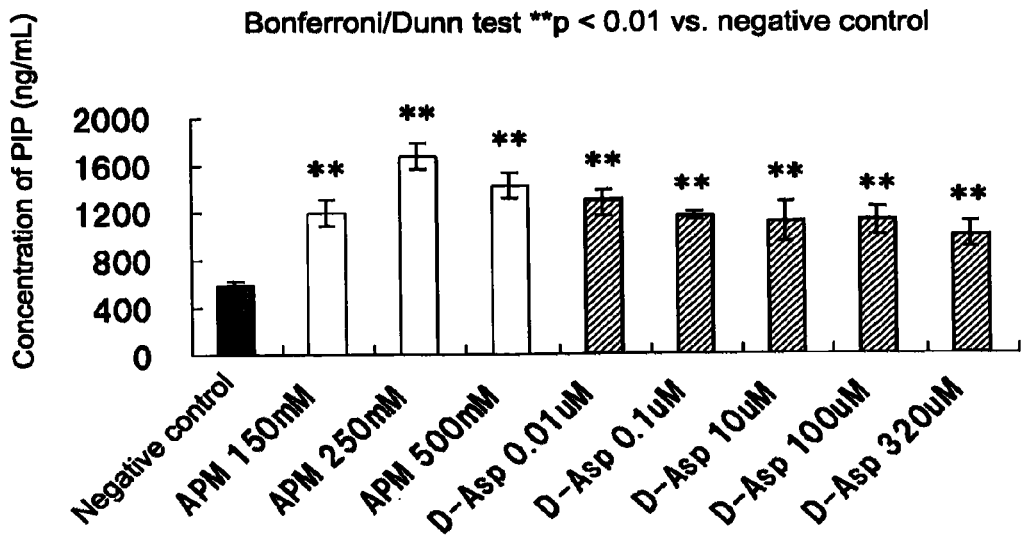
FIG. 1 is a graph illustrating the effect of D-aspartic acid on type I collagen production in normal human dermal fibroblasts.

FIG. 1 shows the results of the experiment examining the effect of adding D-aspartic acid on type I collagen production in human neonatal dermal fibroblasts. The error bars for each experimental condition indicate the standard deviations of the experimentally measured values obtained by repeating the experiment four to six times under the identical condition. Further, the double asterisk (**) indicates that p is less than 1% by Bonferroni/Dunn test.

The PIP concentration was 583 ng/mL in the negative control. When APM had been added at the concentration of 150 μM (micro-molar), 250 μM (micro-molar), and 500 μM (micro-molar) (i.e., positive controls), the PIP concentrations were increased to 1183 ng/mL, 1666 ng/mL, and 1416 ng/mL, respectively. When D-aspartic acid had been added at the concentrations of 0.01 μM (micro-molar), 0.1 μM (micro-molar), 10 μM (micro-molar), 100 μM (micro-molar), and 320 μM (micro-molar), the PIP concentrations were 1286 ng/mL, 1159 ng/mL, 1117 ng/mL, 1119 ng/mL, and 1007 ng/mL, respectively. Thus, compared to the negative control, the medium added with APM or D-aspartic acid showed the statistically significant effect on promoting type I collagen production under the every concentration condition. Further, the effect on promoting type I collagen production of D-aspartic acid at the concentrations of 0.01 μM (micro-molar) to 100 μM (micro-molar) was similar to the effect obtained by using APM at the lowest concentration, i.e., 150 μM (micro-molar), and therefore, it was found that D-aspartic acid had prominently more potent effect on promoting type I collagen production than APM.

Example 2

Effect of Promoting Collagen Production of D-Alanine Methods

The cell culture, addition of amino acids, and quantification of production amount of type I collagen were carried out in the same manner as the Example 1. As an amino acid, D-alanine (manufactured by Peptide Institute, Inc., 2801) was used at the concentrations of 0.01 μM (micro-molar), 0.1 μM (micro-molar), 10 μM (micro-molar), 1000 μM (micro-molar), and 17400 μM (micro-molar). Further, the low-serum medium described above to which neither APM nor D-alanine had been added was employed as a negative control.

Quantification Results

Figure 2:
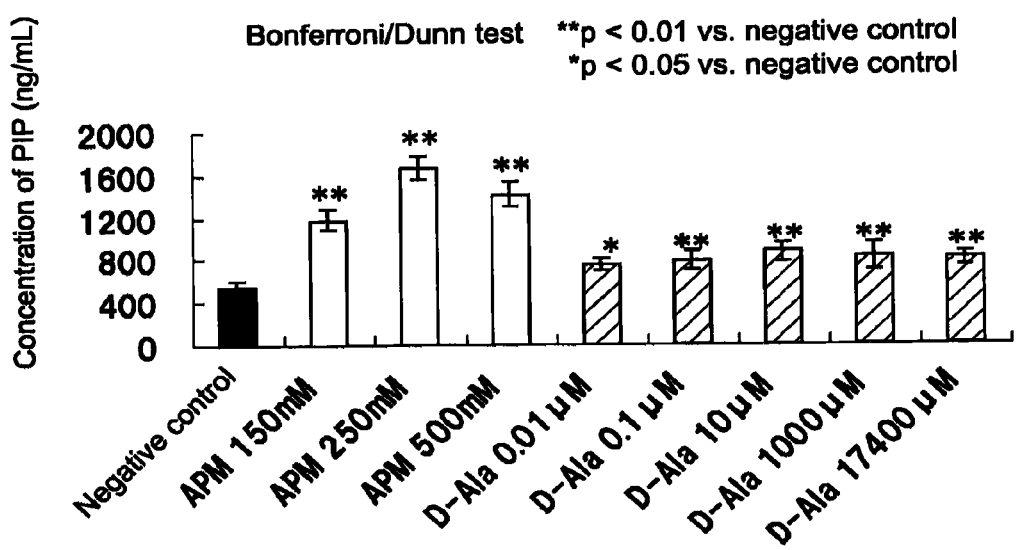
FIG. 2 is a graph illustrating the effect of D-alanine on type I collagen production in normal human dermal fibroblasts.

FIG. 2 shows the results of experiment examining the effect of adding D-alanine on type I collagen production in human neonatal dermal fibroblasts. The error bars for each experimental condition indicate the standard deviations of experimentally measured values obtained by repeating the experiment four to six times under the identical condition. The asterisk (*) indicates that p is less than 5% by Bonferroni/Dunn test. The double asterisk (**) indicates that p is less than 1% by Bonferroni/Dunn test.

The PIP concentration was 551 ng/mL in the negative control. When APM had been added at the concentrations of 150 μM (micro-molar), 250 μM (micro-molar), and 500 μM (micro-molar) (i.e., positive controls), the PIP concentrations were increased to 1183 ng/mL, 1666 ng/mL, and 1416 ng/mL, respectively, illustrating promoted production of type I collagen. When D-alanine had been added at the concentrations of 0.01 μM (micro-molar), 0.1 μM (micro-molar), 10 μM (micro-molar), 1000 μM (micro-molar), and 17400 μM (micro-molar), the PIP concentrations were 750 ng/mL, 789 ng/mL, 876 ng/mL, 823 ng/mL, and 799 ng/mL, respectively. Thus, compared to the negative control, the medium added with APM or D-alanine illustrated the statistically significant effect on promoting type I collagen production under the every concentration condition.

Example 3

Effect on Promoting Collagen Production of L- and D-Aspartic Acid

Methods

The cell culture, addition of amino acids, and quantification of production amount of type I collagen were carried out in the same manner as the Example 1. D-Aspartic acid (manufactured by Wako Pure Chemical Industries, Ltd., 018-04821) of 0.1 μM (micro-molar) and L-aspartic acid (manufactured by Wako Pure Chemical Industries, Ltd., 013-04832) of 0.1 μM (micro-molar) were used as amino acids. Further, the low-serum medium described above to which neither L-aspartic acid nor D-aspartic acid had been added was employed as a negative control.

Quantification Results

Figure 3:
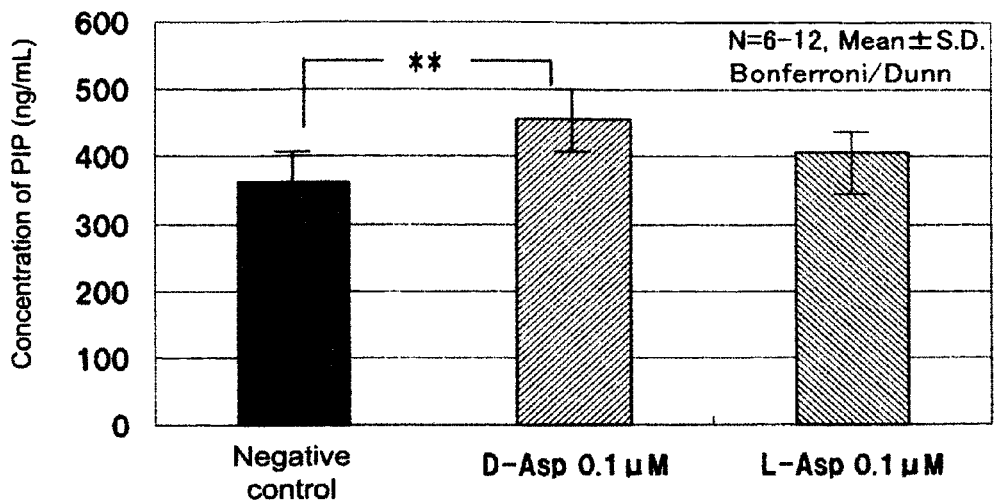
FIG. 3 is a graph illustrating the effect of L- and D-aspartic acid on type I collagen production in normal human dermal fibroblasts.

FIG. 3 shows the results of experiment examining the effect of adding L- and D-aspartic acid on the type I collagen production in human neonatal dermal fibroblasts. The error bars for each experimental condition indicate the standard deviations of experimentally measured values obtained by repeating the experiment six to twelve times under the identical condition. The double asterisk (**) indicates that p is less than 1% by Bonferroni/Dunn test.

The PIP concentration was 361 ng/mL in the negative control. When L-aspartic acid and D-aspartic acid had been at the concentration of 0.1 μM (micro-molar), the PIP concentration was 406 ng/mL and 456 ng/mL, respectively. Based on these results, it was found that production of type I collagen was promoted with statistical significance by addition of 0.1 μM (micro-molar) D-aspartic acid, but not by addition of 0.1 μM (micro-molar) L-aspartic acid.

Example 4

Effect on Promoting Collagen Production of L- and D-Alanine

Methods

The cell culture, addition of amino acids, and quantification of production amount of type I collagen were carried out in the same manner as the Example 1. D-Alanine (manufactured by Peptide Institute, Inc., 2801) of 0.1 μM (micro-molar) or 150 μM (micro-molar) and L-alanine (manufactured by Peptide Institute, Inc., 2701) of 0.1 μM (micro-molar) or 150 μM (micro-molar) were used as amino acids. Further, the low-serum medium described above to which neither L-alanine nor D-alanine had been added was employed as a negative control.

Quantification Results

Figure 4:
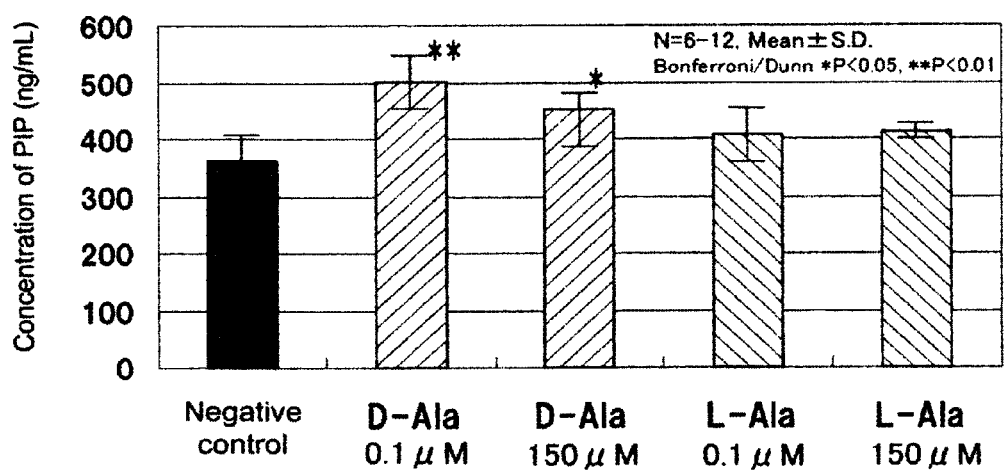
FIG. 4 is a graph illustrating the effect of L- and D-alanine on type I collagen production in normal human dermal fibroblasts.

FIG. 4 shows the results of experiment examining the effect of adding L- and D-alanine on the type I collagen production in human neonatal dermal fibroblasts. The error bars for each experimental condition indicate the standard deviations of experimentally measured values obtained by repeating the experiment six to twelve times under the identical condition. The asterisk (*) and double asterisk (**) indicate that p is less than 5% and less than 1%, respectively, by Bonferroni/Dunn test.

The PIP concentration was 361 ng/mL in the negative control. When D-alanine had been added at the concentrations of 0.1 μM (micro-molar) and 150 μM (micro-molar), the PIP concentrations were 502 ng/mL and 450 ng/mL, respectively. When L-alanine had been added at the concentrations of 0.1 μM (micro-molar) and 150 μM (micro-molar), the PIP concentrations were 405 ng/mL and 413 ng/mL, respectively. Based on these results, it was found that the production of type I collagen was promoted with statistical significance by addition of 0.1 μM (micro-molar) or 150 μM (micro-molar) D-alanine, but not by addition of 0.1 μM (micro-molar) or 150 μM (micro-molar) L-alanine.

Example 5

Effect on Promoting Collagen Production of D-Aspartic Acid and D-Alanine

Methods

The cell culture and addition of amino acids were carried out in the same manner as the Example 1. D-Aspartic acid (manufactured by Wako Pure Chemical Industries, Ltd., 018-04821) of 0.1 μM (micro-molar) and D-alanine (manufactured by Peptide Institute, Inc., 2801) of 0.1 μM (micro-molar) or 0.001 μM (micro-molar) were used as amino acids. Further, the low-serum medium described above to which neither D-aspartic acid nor D-alanine had been added was employed as a negative control. As a positive control, APM was added to the low-serum medium described above to have the concentration of 250 μM (micro-molar). In order to evaluate the production amount of type I collagen, type I procollagen and tropocollagen produced by human neonatal dermal fibroblasts were treated with pepsin (800 to 2500 unit/mg, P7000, manufactured by SIGMA), and the concentration of type I atelocollagen was measured by type I human collagen ELISA (EC1-E105, manufactured by AC Biotechnologies) according to the manufacturer's instruction.

Quantification Results (1)

Figure 5:
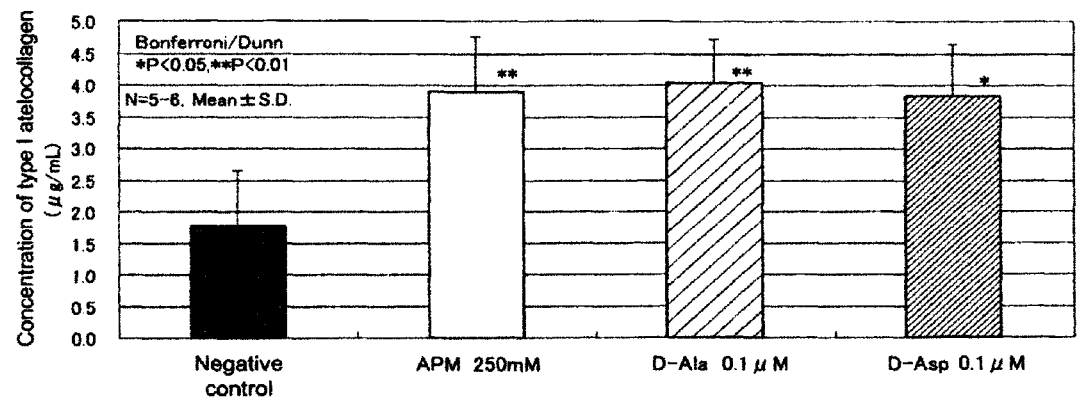
FIG. 5 is a graph illustrating the effect of D-aspartic acid and D-alanine on type I atelocollagen production in normal human dermal fibroblasts.

FIG. 5 shows the results of experiment examining the effect of adding D-aspartic acid and D-alanine on type I atelocollagen production in human neonatal dermal fibroblasts. The error bars for each experimental condition indicate the standard deviations of experimentally measured values obtained by repeating the experiment five to six times under the identical condition. The asterisk (*) and double asterisk (**) indicate that p is less than 5% and less than 1%, respectively, by Bonferroni/Dunn test.

The concentration of type I atelocollagen was 1.8 μg (microgram)/mL in the negative control. When APM had been added at the concentration of 250 mM (i.e., positive control), the concentration of type I atelocollagen was increased to 3.9 μg (microgram)/mL, exhibiting the promoted production of type I collagen. When D-alanine had been added at the concentration of 0.1 μM (micro-molar), the concentration of type I atelocollagen was 4.0 μg (microgram)/mL. When D-aspartic acid had been added at the concentration of 0.1 μM (micro-molar), the concentration of type I atelocollagen was 3.8 μg (microgram)/mL. Based on these results, it was found that the production of type I collagen was promoted with statistical significance by addition of 0.1 μM (micro-molar) D-aspartic acid or D-alanine.

Quantification Results (2)

Figure 6:
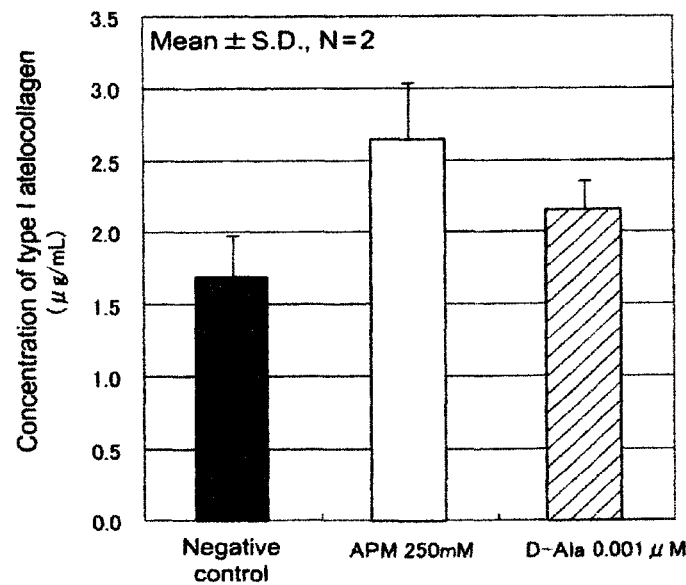
FIG. 6 is a graph illustrating the effect of D-alanine on type I atelocollagen production in normal human dermal fibroblasts.

FIG. 6 shows the results of experiment examining the effect of adding D-alanine on the type I atelocollagen production in human neonatal dermal fibroblasts. The error bars for each experimental condition indicate the standard deviations of experimentally measured values obtained by repeating the experiment two times under the identical condition.

The concentration of type I atelocollagen was 1.7 (microgram)/mL in the negative control. When APM was added at the concentration of 250 mM (i.e., positive control), the concentration of type I atelocollagen was increased to 2.6 μg (microgram)/mL, exhibiting the promoted production of type I collagen. When D-alanine was added at the concentration of 0.001 μM (micro-molar), the concentration of type I atelocollagen was 2.1 μg (microgram)/mL.

Example 6

Formulation examples of a composition comprising D-aspartic acid and/or D-alanine according to the present invention, i.e., an emulsion preparation, a patch, a tablet, a soft capsule, a granule, a beverage, a candy, a cookie, bean paste, a French dressing, a mayonnaise, a French bread, a soy sauce, yogurt, dried seasoning powder for rice, seasoning/sauce for natto, natto, unrefined black vinegar, cream, body cream, gel, a peel-off mask, a wet pack, an emulsion, a skin lotion, and an aerosol preparation, are given below. These formulation examples are all illustrative and not intended to limit the technical scope of the present invention.

Formulation Example 1

Emulsion Preparation

| (Composition) | Content (% by mass) |
| --- | --- |
| D-Aspartic acid | 0.4 |
| Behenyl alcohol | 0.2 |
| Cetanol | 0.5 |
| Glycerin monofatty acid ester | 1.8 |
| Hydrogenated castor oil POE (60) | 1.0 |
| White petrolatum | 2.0 |
| Liquid paraffin | 10.0 |
| Isopropyl myristate | 3.0 |
| Methyl polysiloxane (6cs) | 1.5 |
| Concentrated glycerin | 13.0 |
| Dipropylene glycol | 2.0 |
| Carboxyvinyl polymer | 0.25 |
| Sodium hyaluronate | 0.005 |
| Potassium hydroxide | Proper quantity |
| Lactic acid | Proper quantity |
| Edetate sodium | Proper quantity |
| Ethylparaben | Proper quantity |
| Purified water | Remainder |
| | 100.000 |

Formulation Example 2

Emulsion Preparation

| (Composition) | Content (% by mass) |
| --- | --- |
| D-Alanine | 10 |
| Behenyl alcohol | 0.2 |
| Cetanol | 0.5 |
| Glycerin monofatty acid ester | 1.8 |
| Hydrogenated castor oil POE (60) | 1.0 |
| White petrolatum | 2.0 |
| Liquid paraffin | 10.0 |
| Isopropyl myristate | 3.0 |
| Methyl polysiloxane (6cs) | 1.5 |
| Concentrated glycerin | 13.0 |
| Dipropylene glycol | 2.0 |
| Carboxyvinyl polymer | 0.25 |
| Sodium hyaluronate | 0.005 |
| Potassium hydroxide | Proper quantity |
| Lactic acid | Proper quantity |
| Edetate sodium | Proper quantity |
| Ethylparaben | Proper quantity |
| Purified water | Remainder |
| | 100.000 |

Formulation Example 3

Patch

| (Composition) | Content (% by mass) |
| --- | --- |
| D-Aspartic acid | 0.3 |
| Polyacrylic acid | 3.0 |
| Sodium polyacrylate | 2.5 |
| Gelatin | 0.5 |
| Sodium carboxymethyl cellulose | 4.0 |
| Polyvinyl alcohol | 0.3 |
| Concentrated glycerin | 14.0 |
| 1,3-Butylene glycol | 12.0 |
| Aluminum hydroxide | 0.1 |

-continued

| (Composition) | Content (% by mass) |
|---|---|
| Edetate sodium | 0.03 |
| Methylparaben | 0.1 |
| Purified water | Remainder |
| | 100.00 |

Formulation Example 4

Patch

| (Composition) | Content (% by mass) |
|---|---|
| D-Alanine | 15.0 |
| Polyacrylic acid | 3.0 |
| Sodium polyacrylate | 2.5 |
| Gelatin | 0.5 |
| Sodium carboxymethyl cellulose | 4.0 |
| Polyvinyl alcohol | 0.3 |
| Concentrated glycerin | 14.0 |
| 1,3-Butylene glycol | 12.0 |
| Aluminum hydroxide | 0.1 |
| Edetate sodium | 0.03 |
| Methylparaben | 0.1 |
| Purified water | Remainder |
| | 100.00 |

Formulation Example 5

Tablet

| (Composition) | Content (mg/tablet) |
|---|---|
| D-Aspartic acid and/or D-alanine | 360.5 |
| Lactose | 102.4 |
| Calcium carboxymethyl cellulose | 29.9 |
| Hydroxypropyl cellulose | 6.8 |
| Magnesium stearate | 5.2 |
| Crystalline cellulose | 10.2 |
| | 515.0 |

Formulation Example 6

Tablet

| (Composition) | Content (mg/tablet) |
|---|---|
| Sucrose ester | 70 |
| Crystalline cellulose | 74 |
| Methyl cellulose | 36 |
| Glycerin | 25 |
| D-Aspartic acid and/or D-alanine | 475 |
| N-Acetylglucosamine | 200 |
| Hyaluronic acid | 150 |

-continued

| (Composition) | Content (mg/tablet) |
|---|---|
| Vitamin E | 30 |
| Vitamin B6 | 20 |
| Vitamin B2 | 10 |
| α(alpha)-Lipoic acid | 20 |
| Coenzyme Q10 | 40 |
| Ceramide (Konjac extract) | 50 |
| L-Proline | 300 |
| | 1500 |

Formulation Example 7

Soft Capsule

| (Composition) | Content (mg/capsule) |
|---|---|
| Edible soybean oil | 530 |
| Eucommia ulmoides extract | 50 |
| Ginseng extract | 50 |
| D-Aspartic acid and/or D-alanine | 100 |
| Royal jelly | 50 |
| Maca | 30 |
| GABA | 30 |
| Beeswax | 60 |
| Gelatin | 375 |
| Glycerin | 120 |
| Glycerin fatty acid ester | 105 |
| | 1500 |

Formulation Example 8

Soft Capsule

| (Composition) | Content (mg/capsule) |
|---|---|
| Brown rice germ oil | 659 |
| D-Aspartic acid and/or D-alanine | 500 |
| Resveratrol | 1 |
| Lotus germ extract | 100 |
| Elastin | 180 |
| DNA | 30 |
| Folic acid | 30 |
| | 1500 |

Formulation Example 9

Granule

| (Composition) | Content (mg/pack) |
|---|---|
| D-Aspartic acid and/or D-alanine | 400 |
| Vitamin C | 100 |
| Soybean isoflavone | 250 |
| Reduced lactose | 300 |
| Soybean oligosaccharide | 36 |
| Erythritol | 36 |

-continued

| (Composition) | Content (mg/pack) |
|---|---|
| Dextrin | 30 |
| Flavoring agent | 24 |
| Citric acid | 24 |
| | 1200 |

Formulation Example 10

Beverage

| (Composition) | Content (g/60 mL) |
|---|---|
| Eucommia ulmoides extract | 1.6 |
| Ginseng extract | 1.6 |
| D-Aspartic acid | 0.2 |
| Reduced maltose syrup | 28 |
| Erythritol | 8 |
| Citric acid | 2 |
| Flavoring agent | 1.3 |
| N-Acetylglucosamine | 1 |
| Sodium hyaluronate | 0.5 |
| Vitamin E | 0.3 |
| Vitamin B6 | 0.2 |
| Vitamin B2 | 0.1 |
| α (alpha)-Lipoic acid | 0.2 |
| Coenzyme Q10 | 1.2 |
| Ceramide (Konjac extract) | 0.4 |
| L-proline | 2 |
| Purified water | Remainder |
| | 60 |

Formulation Example 11

Beverage

| (Composition) | Content (g/60 mL) |
|---|---|
| Eucommia ulmoides extract | 1.6 |
| Ginseng extract | 1.6 |
| D-Alanine | 8 |
| Reduced maltose syrup | 28 |
| Erythritol | 8 |
| Citric acid | 2 |
| Flavoring agent | 1.3 |
| N-Acetylglucosamine | 1 |
| Sodium hyaluronate | 0.5 |
| Vitamin E | 0.3 |
| Vitamin B6 | 0.2 |
| Vitamin B2 | 0.1 |
| α (alpha)-Lipoic acid | 0.2 |
| Coenzyme Q10 | 1.2 |
| Ceramide (Konjac extract) | 0.4 |
| L-proline | 2 |
| Purified water | Remainder |
| | 60 |

Formulation Example 12

Candy

| (Composition) | Content (% by mass) |
|---|---|
| Sugar | 50 |
| Syrup | 48 |
| D-Aspartic acid and/or D-alanine | 1 |
| Flavoring agent | 1 |
| | 100 |

Formulation Example 13

Cookie

| (Composition) | Content (% by mass) |
|---|---|
| Weak flour | 45.0 |
| Butter | 17.5 |
| Granulated sugar | 20.0 |
| D-Aspartic acid and/or D-alanine | 4.0 |
| Egg | 12.5 |
| Flavoring agent | 1.0 |
| | 100.0 |

Method for Producing Formulation Example 13 (Cookie)

Granulated sugar is added in portions to butter while stirring, to which an egg, D-aspartic acid and/or D-alanine and a flavoring agent are added and stirred. After mixing thoroughly, uniformly sieved weak flour is added and stirred at a low speed, and allowed to stand as a bulk in a refrigerator. Thereafter, it is molded and baked for 15 minutes at 170° C. (degrees Celsius) to obtain a cookie.

Formulation Example 14

Bean Paste

| (Composition) | Content (g) |
|---|---|
| Soybean | 1000 |
| Malted rice | 1000 |
| Salt | 420 |
| D-Aspartic acid and/or D-alanine | 158 |
| Water | Remainder |
| | 4000 |

Method for Producing Formulation Example 14 (Bean Paste)

Malted rice is mixed thoroughly with a salt. Washed soybeans are soaked overnight in three times its volumes of water, which are then drained off, and new water is added while boiling, and poured into a colander to collect the broth (tanemizu fluid), to which D-aspartic acid and/or D-alanine are dissolved at 10% w/v. The boiled beans are minced immediately, combined with malted rice mixed with salt, to which the tanemizu fluid containing D-aspartic acid and/or D-alanine dissolved therein is added and kneaded evenly to obtain a clay-like hardness. Dumplings are made and stuffed in a container compactly without forming any voids, and the surface of the content is smoothened and sealed with a plastic film. After three months, the content is transferred to a new container and the surface is smoothened and sealed with a plastic film. Instead of adding D-aspartic acid and/or D-alanine to the tanemizu fluid, malted rice producing a large amount of D-aspartic acid and/or D-alanine may be employed. Such malted rice can be selected by quantifying D-aspartic acid and/or D-alanine by the method described in Japanese Patent Unexamined Publication No. 2008-185558. Alternatively, a commercially available bean paste can be supplemented with D-aspartic acid and/or D-alanine or a salt thereof.

Formulation Example 15

French Dressing

| (Composition) | Content (g) |
| --- | --- |
| Salad oil | 27.45 |
| Vinegar | 30.45 |
| Sodium chloride | 0.9 |
| D-Aspartic acid | 0.2 |
| Pepper | 1.0 |
| | 60.0 |

Formulation Example 16

French Dressing

| (Composition) | Content (g) |
| --- | --- |
| Salad oil | 27.0 |
| Vinegar | 30.0 |
| Sodium chloride | 0.9 |
| D-Alanine | 1.1 |
| Pepper | 1.0 |
| | 60.0 |

Method for Producing Formulation Example 15 and 16 (French Dressing)

Vinegar is combined with sodium chloride and D-aspartic acid or D-alanine, and then stirred thoroughly to be dissolved. Salad oil is added to the mixture and the mixture is stirred thoroughly and then pepper is added.

Formulation Example 17

Mayonnaise

| (Composition) | Content (g) |
| --- | --- |
| Salad oil | 134.5 |
| Vinegar | 5 |
| Sodium chloride | 0.9 |
| D-Aspartic acid | 0.5 |
| Egg yolk | 18 |
| Sugar | 0.2 |
| Pepper | 0.9 |
| | 160.0 |

Formulation Example 18

Mayonnaise

| (Composition) | Content (g) |
| --- | --- |
| Salad oil | 134.0 |
| Vinegar | 5 |
| Sodium chloride | 0.9 |
| D-Alanine | 1 |
| Egg yolk | 18 |
| Sugar | 0.2 |
| Pepper | 0.9 |
| | 160.0 |

Method for Producing Formulation Example 17 and 18 (Mayonnaise)

An egg yolk (room temperature) is combined with vinegar, sodium chloride, D-aspartic acid or D-alanine, and pepper, and stirred thoroughly using a whipping apparatus. Stirring is continued while adding salad oil in portions to form an emulsion. Finally, sugar is added and the mixture is stirred.

Formulation Example 19

French Bread

| (Composition) | Content (g) |
| --- | --- |
| Hard flour | 140 |
| Weak flour | 60 |
| Sodium chloride | 3 |
| Sugar | 6 |
| D-Aspartic acid | 2 |
| Dry yeast | 4 |
| Lukewarm water | 128 |
| | 343 |

Formulation Example 20

French Bread

| (Composition) | Content (g) |
| --- | --- |
| Hard flour | 140 |
| Weak flour | 60 |
| Sodium chloride | 3 |
| Sugar | 6 |
| D-Alanine | 17 |

-continued

| (Composition) | Content (g) |
|---|---|
| Dry yeast | 4 |
| Lukewarm water | 120 |
| | 350 |

Method for Producing Formulation Example 19 and 20 (French Bread)

Lukewarm water is combined with 1 g of sugar and dry yeast, which is then allowed to undergo a pre-fermentation. Hard flour, weak flour, sodium chloride, 5 g of sugar, and D-aspartic acid or D-alanine are placed in a bowl, into which the pre-fermented yeast is placed. After kneading thoroughly into a ball-like dough, a primary fermentation is conducted at 30° C. (degrees Celsius). The dough is kneaded again and allowed to stand, and then shaped into suitable forms, which are subjected to a final fermentation using an electronic fermentation machine. After forming coupes, baking is conducted for 30 minutes in an oven at 220° C. (degrees Celsius).

Formulation Example 21

Soy Sauce

| (Composition) | Content (g) |
|---|---|
| Commercially available soy sauce | 996 |
| D-Aspartic acid | 4 |
| | 1000 |

Formulation Example 22

Soy Sauce

| (Composition) | Content (g) |
|---|---|
| Commericially available soy sauce | 900 |
| D-Alanine | 100 |
| | 1000 |

Method for Producing Formulation Example 21 and 22 (Soy Sauce)

Commercially available soy sauce is supplemented with D-aspartic acid or D-alanine, and stirred thoroughly. Instead of adding D-aspartic acid or D-alanine, or a salt thereof, malted rice producing a large amount of D-aspartic acid or D-alanine may be employed for fermenting soy sauce. Such malted rice can be selected by quantifying D-aspartic acid or D-alanine by the method described in Japanese Patent Unexamined Publication No. 2008-185558.

Formulation Example 23

Yogurt

| (Composition) | Content (g) |
|---|---|
| Milk | 898 |
| L. bulgaricus | 50 |
| S. thermophilus | 50 |
| D-Aspartic acid | 2 |
| | 1000 |

Formulation Example 24

Yogurt

| (Composition) | Content (g) |
|---|---|
| Milk | 850 |
| L. bulgaricus | 50 |
| S. thermophilus | 50 |
| D-Alanine | 50 |
| | 1000 |

Method for Producing Formulation Example 23 and 24 (Yogurt)

Fermentation is conducted at 40 to 45° C. (degrees Celsius). Other commercially available fermentation seed organisms may be employed and commercially available yogurt may be supplemented with D-aspartic acid or D-alanine. Instead of adding D-aspartic acid or D-alanine, or a salt thereof, a seed organism producing a large amount of D-aspartic acid or D-alanine may be employed. Such an organism can be selected by quantifying D-aspartic acid or D-alanine by the method described in Japanese Patent Unexamined Publication No. 2008-185558.

Formulation Example 25

Dried Seasoning Powder for Rice

| (Composition) | Content (g) |
|---|---|
| D-Aspartic acid and/or D-alanine | 50 |
| Laver | 15 |
| Sodium L-glutamate | 10 |
| Sodium chloride | 2 |
| Roasted sesame | 10 |
| Dried mackerel shavings | 10 |
| Sugar | 1 |
| Soy sauce | 2 |
| | 100 |

Formulation Example 26

Seasoning/Sauce for Natto

| (Composition) | Content (g) |
|---|---|
| Commercially available sauce for natto | 9.8 |
| D-Aspartic acid | 0.2 |
| | 10 |

Formulation Example 27

Seasoning/Sauce for Natto

| (Composition) | Content (g) |
|---|---|
| Commercially available sauce for natto | 9 |
| D-Alanine | 1 |
| | 10 |

Formulation Example 28

Natto

| (Composition) | Content (g) |
|---|---|
| Commercially available natto | 19.9 |
| D-Aspartic acid and/or D-alanine | 0.1 |
| | 20 |

Method for Producing Formulation Example 28 (Natto)

Instead of adding D-aspartic acid and/or D-alanine, or a salt thereof, an organism producing a large amount of D-aspartic acid and/or D-alanine may be employed for producing natto. Such an organism can be selected by quantifying D-aspartic acid and/or D-alanine by the method described in Japanese Patent Unexamined Publication No. 2008-185558.

Formulation Example 29

Unrefined Black Vinegar

| (Composition) | Content (g) |
|---|---|
| Commercially available unrefined black vinegar | 996 |
| D-Aspartic acid | 4 |
| | 1000 |

Formulation Example 30

Unrefined Black Vinegar

| (Composition) | Content (g) |
|---|---|
| Commercially available unrefined black vinegar | 900 |
| D-Alanine | 100 |
| | 1000 |

Method for Producing Formulation Example 29 and 30 (Unrefined Black Vinegar)

Instead of adding D-aspartic acid or D-alanine, or a salt thereof, an organism producing a large amount of D-aspartic acid or D-alanine may be employed for producing vinegar, black vinegar or unrefined vinegar. Such an organism can be selected by quantifying D-aspartic acid or D-alanine by the method described in Japanese Patent Unexamined Publication No. 2008-185558.

Formulation Example 31

Cream

| (Composition) | Content (% by mass) |
|---|---|
| Liquid paraffin | 3 |
| White petrolatum | 1 |
| Dimethyl polysiloxane | 1 |
| Stearyl alcohol | 1.8 |
| Behenyl alcohol | 1.6 |
| Glycerin | 8 |
| Dipropylene glycol | 5 |
| Macadamia nut oil | 2 |
| Hydrogenated oil | 3 |
| Squalane | 6 |
| Stearic acid | 2 |
| Cholesteryl hydroxystearate | 0.5 |
| Cetyl 2-ethylhexanoate | 4 |
| Polyoxyethylene hydrogenated castor oil | 0.5 |
| Self-emulsifying glyceryl monostearate | 3 |
| Potassium hydroxide | 0.15 |
| Sodium hexametaphosphate | 0.05 |
| Trimethyl glycine | 2 |
| Potassium ascorbyl tocopheryl phosphate | 1 |
| Tocopheryl acetate | 0.1 |
| D-Aspartic acid | 0.4 |
| Paraben | Proper quantity |
| Edetate trisodium | 0.05 |
| 4-t-Butyl-4'-methoxy dibenzoylmethane | 0.05 |
| Glyceryl ethylhexanoate dimethoxycinnamate | 0.05 |
| Colorant | Proper quantity |
| Carboxyvinyl polymer | 0.05 |
| Purified water | Remainder |
| | 100.00 |

Formulation Example 32

Cream

| (Composition) | Content (% by mass) |
|---|---|
| Liquid paraffin | 3 |
| White petrolatum | 1 |
| Dimethyl polysiloxane | 1 |
| Stearyl alcohol | 1.8 |
| Behenyl alcohol | 1.6 |
| Glycerin | 8 |
| Dipropylene glycol | 5 |
| Macadamia nut oil | 2 |
| Hydrogenated oil | 3 |
| Squalane | 6 |
| Stearic acid | 2 |
| Cholesteryl hydroxystearate | 0.5 |
| Cetyl 2-ethylhexanoate | 4 |
| Polyoxyethylene hydrogenated castor oil | 0.5 |
| Self-emulsifying glyceryl monostearate | 3 |
| Potassium hydroxide | 0.15 |
| Sodium hexametaphosphate | 0.05 |
| Trimethyl glycine | 2 |
| Potassium ascorbyl tocopheryl phosphate | 1 |
| Tocopheryl acetate | 0.1 |
| D-Alanine | 10 |
| Paraben | Proper quantity |
| Edetate trisodium | 0.05 |
| 4-t-Butyl-4'-methoxy dibenzoylmethane | 0.05 |
| Glyceryl ethylhexanoate dimethoxycinnamate | 0.05 |
| Colorant | Proper quantity |
| Carboxyvinyl polymer | 0.05 |
| Purified water | Remainder |
| | 100.00 |

Formulation Example 33

Body Cream

| (Composition) | Content (% by mass) |
|---|---|
| Dimethyl polysiloxane | 3 |
| Decamethyl cyclopentasiloxane | 13 |
| Dodecamethyl cyclohexasiloxane | 12 |
| Polyoxyethylene methylpolysiloxane copolymer | 1 |
| Ethanol | 2 |
| Isopropanol | 1 |
| Glycerin | 3 |
| Dipropylene glycol | 5 |
| Polyethylene glycol 6000 | 5 |
| Sodium hexametaphosphate | 0.05 |
| Tocopheryl acetate | 0.1 |
| D-Aspartic acid | 0.4 |
| *Foeniculum vulgare* (Fennel) extract | 0.1 |
| *Hamamelis virginiana* (Witch Hazel) extract | 0.1 |
| Ginseng extract | 0.1 |
| L-Menthol | Proper quantity |
| Paraoxybenzoic acid ester (Paraben) | Proper quantity |
| Edetate trisodium | 0.05 |
| Dimorpholinopyridazinone | 0.01 |
| Isopentyl trimethoxycinnamate trisiloxane | 0.1 |
| Iron oxide yellow | Proper quantity |
| Cobalt titanate | Proper quantity |
| Dimethyl distearyl ammonium hectorite | 1.5 |
| Polyvinyl alcohol | 0.1 |
| Hydroxyethyl cellulose | 0.1 |
| Trimethylsiloxysilicate | 2 |
| Flavoring agent | Proper quantity |
| Purified water | Remainder |
| | 100.00 |

Formulation Example 34

Body Cream

| (Composition) | Content (% by mass) |
|---|---|
| Dimethyl polysiloxane | 3 |
| Decamethyl cyclopentasiloxane | 13 |
| Dodecamethyl cyclohexasiloxane | 12 |
| Polyoxyethylene methylpolysiloxane copolymer | 1 |
| Ethanol | 2 |
| Isopropanol | 1 |
| Glycerin | 3 |
| Dipropylene glycol | 5 |
| Polyethylene glycol 6000 | 5 |
| Sodium hexametaphosphate | 0.05 |
| Tocopheryl acetate | 0.1 |
| D-Alanine | 10 |
| *Foeniculum vulgare* (Fennel) extract | 0.1 |
| *Hamamelis virginiana* (Witch Hazel) extract | 0.1 |
| Ginseng extract | 0.1 |
| L-Menthol | Proper quantity |
| Paraoxybenzoic acid ester (Paraben) | Proper quantity |
| Edetate trisodium | 0.05 |
| Dimorpholinopyridazinone | 0.01 |
| Isopentyl trimethoxycinnamate trisiloxane | 0.1 |
| Iron oxide yellow | Proper quantity |
| Cobalt titanate | Proper quantity |
| Dimethyl distearyl ammonium hectorite | 1.5 |
| Polyvinyl alcohol | 0.1 |
| Hydroxyethyl cellulose | 0.1 |
| Trimethylsiloxysilicate | 2 |
| Flavoring agent | Proper quantity |
| Purified water | Remainder |
| | 100.00 |

Formulation Example 35

Gel

| (Composition) | Content (% by mass) |
|---|---|
| Dimethyl polysiloxane | 5 |
| Glycerin | 2 |
| 1,3-Butylene glycol | 5 |
| Polyethylene glycol 1500 | 3 |
| Polyethylene glycol 20000 | 3 |
| Cetyl ethylhexanoate | 3 |
| Citric acid | 0.01 |
| Sodium citrate | 0.1 |
| Sodium hexametaphosphate | 0.1 |
| Dipotassium glycyrrhizinate | 0.1 |
| D-Aspartic acid | 0.4 |
| Tocopheryl acetate | 0.1 |
| *Scutellaria Baicalensis* root extract | 0.1 |
| *Saxifraga sarmentos* extract | 0.1 |
| Edetate trisodium | 0.1 |
| Xanthan gum | 0.3 |
| Acrylates/C10-30 alkyl acrylate crosspolymer (Pemulen TR-2) | 0.05 |
| Agar powder | 1.5 |
| Phenoxyethanol | Proper quantity |
| Dibutylhydroxytoluene | Proper quantity |
| Purified water | Remainder |
| | 100.00 |

Formulation Example 36

Gel

| (Composition) | Content (% by mass) |
|---|---|
| Dimethyl polysiloxane | 5 |
| Glycerin | 2 |
| 1,3-Butylene glycol | 5 |
| Polyethylene glycol 1500 | 3 |
| Polyethylene glycol 20000 | 3 |
| Cetyl ethylhexanoate | 3 |
| Citric acid | 0.01 |
| Sodium citrate | 0.1 |
| Sodium hexametaphosphate | 0.1 |
| Dipotassium glycyrrhizinate | 0.1 |
| D-Alanine | 10 |
| Tocopheryl acetate | 0.1 |
| *Scutellaria Baicalensis* root extract | 0.1 |
| *Saxifraga sarmentos* extract | 0.1 |
| Edetate trisodium | 0.1 |
| Xanthan gum | 0.3 |
| Acrylates/C10-30 alkyl acrylate crosspolymer (Pemulen TR-2) | 0.05 |
| Agar powder | 1.5 |
| Phenoxyethanol | Proper quantity |
| Dibutylhydroxytoluene | Proper quantity |
| Purified water | Remainder |
| | 100.00 |

Formulation Example 37

Peel-Off Mask

| (Composition) | Content (% by mass) |
|---|---|
| Ethanol | 10 |
| 1,3-Butylene glycol | 6 |
| Polyethylene glycol 4000 | 2 |
| Olive oil | 1 |
| Macadamia nut oil | 1 |
| Phytosteryl hydroxystearic acid | 0.05 |
| Lactic acid | 0.05 |
| Sodium lactate | 0.1 |
| Disodium ascorbyl sulfate | 0.1 |
| Potassium ascorbyl tocopheryl phosphate | 0.1 |
| D-Aspartic acid | 0.4 |
| Fish collagen | 0.1 |
| Sodium chondroitin sulfate | 0.1 |
| Sodium carboxymethyl cellulose | 0.2 |
| Polyvinyl alcohol | 12 |
| Paraoxybenzoic acid ester (Paraben) | Proper quantity |
| Flavoring agent | Proper quantity |
| Purified water | Remainder |
| | 100.00 |

Formulation Example 38

Peel-Off Mask

| (Composition) | Content (% by mass) |
|---|---|
| Ethanol | 10 |
| 1,3-Butylene glycol | 6 |
| Polyethylene glycol 4000 | 2 |
| Olive oil | 1 |
| Macadamia nut oil | 1 |
| Phytosteryl hydroxystearic acid | 0.05 |
| Lactic acid | 0.05 |
| Sodium lactate | 0.1 |
| Disodium ascorbyl sulfate | 0.1 |
| Potassium ascorbyl tocopheryl phosphate | 0.1 |
| D-Alanine | 15 |
| Fish collagen | 0.1 |
| Sodium chondroitin sulfate | 0.1 |
| Sodium carboxymethyl cellulose | 0.2 |
| Polyvinyl alcohol | 12 |
| Paraoxybenzoic acid ester (Paraben) | Proper quantity |
| Flavoring agent | Proper quantity |
| Purified water | Remainder |
| | 100.00 |

Formulation Example 39

Wet Pack

| (Composition) | Content (% by mass) |
|---|---|
| Glycerin | 1 |
| 1,3-Butylene glycol | 8 |
| Xylit | 2 |
| Polyethylene glycol 1500 | 2 |
| Rosemary oil | 0.01 |
| Sage oil | 0.1 |
| Citric acid | 0.02 |
| Sodium citrate | 0.08 |
| Sodium hexametaphosphate | 0.01 |
| Hydroxypropyl-β(beta)-cyclodextrin | 0.1 |
| D-Aspartic acid | 0.25 |
| Birch extract | 0.1 |
| Lavender oil | 0.01 |
| Xanthane gum | 0.05 |
| Carboxylvinyl polymer | 0.15 |
| Paraoxybenzoic acid ester (Paraben) | Proper quantity |
| Purified water | Remainder |
| | 100.00 |

Formulation Example 40

Wet Pack

| (Composition) | Content (% by mass) |
|---|---|
| Glycerin | 1 |
| 1,3-Butylene glycol | 8 |
| Xylit | 2 |
| Polyethylene glycol 1500 | 2 |
| Rosemary oil | 0.01 |
| Sage oil | 0.1 |
| Citric acid | 0.02 |
| Sodium citrate | 0.08 |
| Sodium hexametaphosphate | 0.01 |
| Hydroxypropyl-β(beta)-cyclodextrin | 0.1 |
| D-Alanine | 8 |
| Birch extract | 0.1 |
| Lavender oil | 0.01 |
| Xanthane gum | 0.05 |
| Carboxylvinyl polymer | 0.15 |
| Paraoxybenzoic acid ester (Paraben) | Proper quantity |
| Purified water | Remainder |
| | 100.00 |

Formulation Example 41

Emulsion

| (Composition) | Content (% by mass) |
|---|---|
| Liquid paraffin | 7 |
| White petrolatum | 3 |
| Decamethyl cyclopentasiloxane | 2 |
| Behenyl alcohol | 1.5 |
| Glycerin | 5 |
| Dipropylene glycol | 7 |
| Polyethylene glycol 1500 | 2 |
| Jojoba oil | 1 |
| Isostearic acid | 0.5 |
| Stearic acid | 0.5 |
| Behenic acid | 0.5 |
| Pentaerythritol tetra (2-ethylhexanoate) | 3 |
| Cetyl 2-ethylhexanoate | 3 |
| Glycerin monostearate | 1 |
| Polyoxyethylene-glycerin monostearate | 1 |
| Potassium hydroxide | 0.1 |
| Sodium hexametaphosphate | 0.05 |
| Stearyl glycyrrhetinate | 0.05 |
| D-Aspartic acid | 0.2 |
| Royal jelly extract | 0.1 |
| Yeast extract | 0.1 |
| Tocopheryl acetate | 0.1 |
| Acetylated sodium hyaluronate | 0.1 |
| Edetate trisodium | 0.05 |
| 4-t-Butyl-4'-methoxydibenzoyl methane | 0.1 |
| 2-Ethylhexyl paramethoxycinnamate | 0.1 |
| Carboxylvinyl polymer | 0.15 |
| Paraben | Proper quantity |
| Flavoring agent | Proper quantity |
| Purified water | Remainder |
| | 100.00 |

Formulation Example 42

Emulsion

| (Composition) | Content (% by mass) |
|---|---|
| Liquid paraffin | 7 |
| White petrolatum | 3 |
| Decamethylpentasiloxane | 2 |
| Behenyl alcohol | 1.5 |
| Glycerin | 5 |
| Dipropylene glycol | 7 |
| Polyethylene glycol 1500 | 2 |
| Jojoba oil | 1 |
| Isostearic acid | 0.5 |
| Stearic acid | 0.5 |
| Behenic acid | 0.5 |
| Pentaerythritol tetra (2-ethylhexanoate) | 3 |
| Cetyl 2-ethylhexanoate | 3 |
| Glycerin monostearate | 1 |
| Polyoxyethylene-glycerin monostearate | 1 |
| Potassium hydroxide | 0.1 |
| Sodium hexametaphosphate | 0.05 |
| Stearyl glycyrrhetinate | 0.05 |
| D-Alanine | 5 |
| Royal jelly extract | 0.1 |
| Yeast extract | 0.1 |
| Tocopheryl acetate | 0.1 |
| Acetylated sodium hyaluronate | 0.1 |
| Edetate trisodium | 0.05 |
| 4-t-Butyl-4'-methoxydibenzoyl methane | 0.1 |
| 2-Ethylhexyl paramethoxycinnamate | 0.1 |
| Carboxylvinyl polymer | 0.15 |

-continued

| (Composition) | Content (% by mass) |
|---|---|
| Paraben | Proper quantity |
| Flavoring agent | Proper quantity |
| Purified water | Remainder |
| | 100.00 |

Formulation Example 43

Emulsion

| (Composition) | Content (% by mass) |
|---|---|
| Dimethyl polysiloxane | 2 |
| Behenyl alcohol | 1 |
| Batyl alcohol | 0.5 |
| Glycerin | 5 |
| 1,3-Butylene glycol | 7 |
| Erythritol | 2 |
| Hydrogenated oil | 3 |
| Squalane | 6 |
| Pentaerythritol tetra (2-ethylhexanoate) | 2 |
| Polyoxyethylene glyceryl isostearate | 1 |
| Polyoxyethylene glyceryl monostearate | 1 |
| D-Aspartic acid | 0.3 |
| Potassium hydroxide | Proper quantity |
| Sodium hexametaphosphate | 0.05 |
| Phenoxyethanol | Proper quantity |
| Carboxylvinyl polymer | 0.1 |
| Purified water | Remainder |
| | 100.00 |

Formulation Example 44

Emulsion

| (Composition) | Content (% by mass) |
|---|---|
| Dimethyl polysiloxane | 2 |
| Behenyl alcohol | 1 |
| Batyl alcohol | 0.5 |
| Glycerin | 5 |
| 1,3-Butylene glycol | 7 |
| Erythritol | 2 |
| Hydrogenated oil | 3 |
| Squalane | 6 |
| Pentaerythritol tetra (2- ethylhexanoate) | 2 |
| Polyoxyethylene glyceryl isostearate | 1 |
| Polyoxyethylene glyceryl monostearate | 1 |
| D-Alanine | 10 |
| Potassium hydroxide | Proper quantity |
| Sodium hexametaphosphate | 0.05 |
| Phenoxyethanol | Proper quantity |
| Carboxylvinyl polymer | 0.1 |
| Purified water | Remainder |
| | 100.00 |

Formulation Example 45

Skin Lotion

| (Composition) | Content (% by mass) |
|---|---|
| Ethyl alcohol | 5 |
| Glycerin | 1 |
| 1,3-Butylene glycol | 5 |
| Polyoxyethylene polyoxypropylene decyl tetradecyl ether | 0.2 |
| Sodium hexametaphosphate | 0.03 |
| Trimethyl glycine | 1 |
| Sodium polyasparaginate | 0.1 |
| Potassium ascorbyl tocopheryl phosphate | 0.1 |
| Thiotaurine | 0.1 |
| D-Aspartic acid | 0.3 |
| Edetate trisodium | 0.1 |
| Carboxylvinyl polymer | 0.05 |
| Potassium hydroxide | 0.02 |
| Phenoxyethanol | Proper quantity |
| Flavoring agent | Proper quantity |
| Purified water | Remainder |
| | 100.00 |

Formulation Example 46

Skin Lotion

| (Composition) | Content (% by mass) |
|---|---|
| Ethyl alcohol | 5 |
| Glycerin | 1 |
| 1,3-Butylene glycol | 5 |
| Potassium ascorbyl tocopheryl phosphate | 0.2 |
| Sodium hexametaphosphate | 0.03 |
| Trimethyl glycine | 1 |
| Sodium polyasparaginate | 0.1 |
| Potassium ascorbyl tocopheryl phosphate | 0.1 |
| Thiotaurine | 0.1 |
| D-Alanine | 10 |
| Edetate trisodium | 0.1 |
| Carboxylvinyl polymer | 0.05 |
| Potassium hydroxide | 0.02 |
| Phenoxyethanol | Proper quantity |
| Flavoring agent | Proper quantity |
| Purified water | Remainder |
| | 100.00 |

Formulation Example 47

Skin Lotion

| (Composition) | Content (% by mass) |
|---|---|
| Ethanol | 10 |
| Dipropylene glycol | 1 |
| Polyethylene glycol 1000 | 1 |

-continued

| (Composition) | Content (% by mass) |
|---|---|
| Polyoxyethylene methyl glucoside | 1 |
| Jojoba oil | 0.01 |
| Glyceryl tri(2-ethylhexanoate) | 0.1 |
| Polyoxyethylene hydrogenated castor oil | 0.2 |
| Polyglyceryl diisostearate | 0.15 |
| Sodium N-stearoyl-L-glutamate | 0.1 |
| Citric acid | 0.05 |
| Sodium citrate | 0.2 |
| Potassium hydroxide | 0.4 |
| Dipotassium glycyrrhizinate | 0.1 |
| Arginine hydrochloride | 0.1 |
| L-Ascorbic acid-2-glucoside | 2 |
| D-Aspartic acid | 0.2 |
| Edetate trisodium | 0.05 |
| Octyl 4-methoxycinnamate | 0.01 |
| Dibutylhydroxy toluene | Proper quantity |
| Paraben | Proper quantity |
| Deep sea water | 3 |
| Flavoring agent | Proper quantity |
| Purified water | Remainder |
| | 100.00 |

Formulation Example 48

Skin Lotion

| (Composition) | Content (% by mass) |
|---|---|
| Ethanol | 10 |
| Dipropylene glycol | 1 |
| Polyethylene glycol 1000 | 1 |
| Polyoxyethylene methyl glucoside | 1 |
| Jojoba oil | 0.01 |
| Glyceryl tri(2-ethylhexanoate) | 0.1 |
| Polyoxyethylene hydrogenated castor oil | 0.2 |
| Polyglyceryl diisostearate | 0.15 |
| Sodium N-stearoyl-L-glutamate | 0.1 |
| Citric acid | 0.05 |
| Sodium citrate | 0.2 |
| Potassium hydroxide | 0.4 |
| Dipotassium glycyrrhizinate | 0.1 |
| Arginine hydrochloride | 0.1 |
| L-Ascorbic acid-2-glucoside | 2 |
| D-Alanine | 12 |
| Edetate trisodium | 0.05 |
| Octyl 4-methoxycinnamate | 0.01 |
| Dibutylhydroxytoluene | Proper quantity |
| Paraben | Proper quantity |
| Deep sea water | 3 |
| Flavoring agent | Proper quantity |
| Purified water | Remainder |
| | 100.00 |

Formulation Example 49

Stock Solution of Aerosol Urea Preparation for External Use

| (Composition) | Content (% by mass) |
|---|---|
| Ethanol | 15.0 |
| Polyoxyethylene hydrogenated castor oil 50 | 1.5 |
| Diphenhydramine | 1.0 |
| Dibucaine | 2.0 |
| Tocopheryl acetate | 0.5 |
| D-Aspartic acid | 0.1 |
| Isostearic acid | 0.1 |
| 1,3-Butylene glycol | 3.0 |
| Polyethylene glycol 400 | 3.0 |
| Camphor | 0.05 |
| Urea | 20.0 |
| Purified water | Remainder |
| | 100.00 |

Formulation Example 50

Stock Solution of Aerosol Urea Preparation for External Use

| (Composition) | Content (% by mass) |
|---|---|
| Ethanol | 15.0 |
| Polyoxyethylene hydrogenated castor oil 50 | 1.5 |
| Diphenhydramine | 1.0 |
| Dibucaine | 2.0 |
| Tocopheryl acetate | 0.5 |
| D-Alanine | 5 |
| Isostearic acid | 0.1 |
| 1,3-Butylene glycol | 3.0 |
| Polyethylene glycol 400 | 3.0 |
| Camphor | 0.05 |
| Urea | 20.0 |
| Purified water | Remainder |
| | 100.00 |

Formulation Example 51

Aerosol Urea Spray

| (Composition) | Content (% by mass) |
|---|---|
| Stock solution of aerosol urea preparation for external use | 65.0 |
| Dimethyl ether | 35.0 |
| | 100.00 |

Method of Filling Formulation Example 51 (Aerosol Urea Spray)

Stock solution of aerosol urea preparation for external use and dimethyl ether are filled in a pressure resistant aerosol aluminum can of which internal surface is coated with Teflon (registered trade mark) to prepare an aerosol preparation.

The invention claimed is:

1. A method of suppressing and/or improving a skin condition caused by reduced collagen production in a subject in need thereof comprising administering to the subject in need thereof a composition comprising a collagen production stimulating composition consisting essentially of D-aspartic acid, D-alanine, and/or salts thereof, wherein the skin condition comprises photoaging and/or wrinkles.

2. The method according to claim 1, wherein the composition is used for an external preparation for the skin.

3. The method according to claim 1, wherein the composition is used for a food composition.

* * * * *